United States Patent [19]

Sher

[11] Patent Number: 5,171,254
[45] Date of Patent: Dec. 15, 1992

[54] EYE FIXATION DEVICE

[76] Inventor: Neal A. Sher, Suite 750, Medical Arts Bldg., Ninth and Nicollet, Minneapolis, Minn. 55402

[21] Appl. No.: 794,446
[22] Filed: Nov. 19, 1991
[51] Int. Cl.$^5$ .................................................. A61B 17/00
[52] U.S. Cl. ...................................... 606/166; 128/20
[58] Field of Search ........................... 606/4–6, 606/130, 161, 166; 128/20; 355/76

[56] References Cited

U.S. PATENT DOCUMENTS

| | | | |
|---|---|---|---|
| 2,702,540 | 2/1955 | Debeh | 128/20 |
| 3,074,407 | 1/1963 | Moon et al. | 128/303 |
| 4,340,059 | 7/1982 | Marinoff | 128/305 |
| 4,412,738 | 11/1983 | Ahern et al. | 355/76 |
| 4,669,870 | 6/1987 | Fosh | 355/76 X |
| 4,688,570 | 8/1987 | Kramer et al. | 128/305 |
| 4,718,418 | 1/1988 | L'Esperance | 128/303 |
| 4,846,173 | 7/1989 | Davidson | 606/130 |
| 4,905,711 | 3/1990 | Bennett et al. | 128/869 |
| 5,009,660 | 4/1991 | Clapham | 606/166 |
| 5,070,860 | 12/1991 | Grounauer | 128/20 |
| 5,092,863 | 3/1992 | Schanzlin | 606/5 |
| 5,108,412 | 4/1992 | Krumeich et al. | 606/4 X |

FOREIGN PATENT DOCUMENTS 372127 6/1990 European Pat. Off. ............ 606/166
WO8706126 10/1987 PCT Int'l Appl. .

OTHER PUBLICATIONS

Medline data base search printout identifying several journal articles relating to fixation devices.

Primary Examiner—Randall L. Green
Assistant Examiner—Mary Beth O. Jones
Attorney, Agent, or Firm—Gregory P. Kaihoi

[57] ABSTRACT

An ophthalmic instrument for fixating a patient's eye during an ophthalmic procedure. The instrument includes a speculum securable against the patient's bony orbit, and a fixation ring attachable to the patient's eye, the ring including both a mechanism for fixating the ring with respect to the eye, and a mechanism for adjustably attaching the ring to the speculum. The instrument may include one or more bubble-type levels carried on the fixation ring for indicating the orientation of the ring and assisting the surgeon in orienting the eye of the patient before securing the ring to the speculum.

15 Claims, 2 Drawing Sheets

EYE FIXATION DEVICE

FIELD OF THE INVENTION

The invention relates to an eye fixation device useful in restraining movement of an eye during ophthalmic procedures.

BACKGROUND OF THE INVENTION

In a variety of surgical procedures on the eye, it is desirable or necessary to prevent the eye from moving. Examples include corneal refractive surgery, corneal laser surgery (e.g., with the 193nm excimer laser), and radial keratotomy. Currently, ophthalmologists often merely use a pair of forceps to stabilize the eye during such procedures. Obviously, this can be less than satisfactory, as it can sometimes be difficult to get a secure grip on the eyeball, squeezing the eye with the forceps can elevate intraocular pressure, thereby temporarily deforming the shape of the cornea (which can adversely affect the procedure being performed), and this technique occupies one of the surgeon's hands, preventing him from using both hands to hold other instruments or hold the patient's head still.

One device that has been proposed for use in fixating the eye of a patient is shown in U.S. Pat. No. 5,009,660 (Clapham). The Clapham device utilizes a vacuum ring carried at the end of a handle which extends away from the vacuum ring at an angle. The vacuum ring can be secured to the eye around the cornea. The device is somewhat cumbersome, however, and still requires the surgeon to hold the device manually to prevent movement of the eye.

U.S. Pat. No. 4,718,418 (L'Esperance) uses a vacuum ring which can be placed on the eye, but the vacuum ring is rigidly connected to an external piece of equipment (in this case, a laser used in treatment of the eye). This technique has inherent dangers, however, in that if the patient should panic or, for whatever reason, attempt to move away from the rigid device, serious trauma to the eye can result.

SUMMARY OF THE INVENTION

The invention provides a fixation device for securing a patient's eye during an ophthalmic procedure. The device includes a speculum for holding the patient's eyelid open, the speculum seating against the bony orbit of the eye. A fixation ring includes means for fixating the ring with respect to the eye (such as by vacuum), and means for adjustably attaching the ring to the speculum.

In use, the speculum is first inserted into the eye and seated against the bony orbit. The fixation ring is then placed concentrically around the cornea (typically seating on the episclera). The surgeon then has the patient look directly at a particular target (to properly align the eye, e.g. with respect to a laser or other operating device), and the fixation ring is then secured to the speculum to immobilize the eye.

In a preferred embodiment, the fixation ring is secured to the speculum by use of a vacuum mechanism. Each of the blades of the speculum include a generally flat top surface having vacuum holes therein, and the fixation ring carries a pair of corresponding attachment plates. When vacuum is applied to the speculum, the attachment plates are secured against the flat top surface of the speculum blades. Alternately, this arrangement could be reversed with vacuum applied through the fixation ring rather than through the speculum blades. Moreover, a similar configuration could be utilized having electromagnets or other equivalent means rather than vacuum to fixate the ring with respect to the speculum.

In another embodiment, the fixation ring includes one or more levels (such as a bubble-type level) for indicating the orientation of the ring. For example, one level can be placed on the side of the ring, and a second can be placed on the top of the ring; as a patient lies on his back, if the ring is secured to the eye exactly concentric with the cornea, the levels would indicate the position of the eye to allow the surgeon to fixate the eye when the plane of the iris is exactly horizontal (i.e., when a plane tangential to the apex of the cornea is exactly horizontal).

BEST MODE FOR CARRYING OUT THE INVENTION

Figure 1:
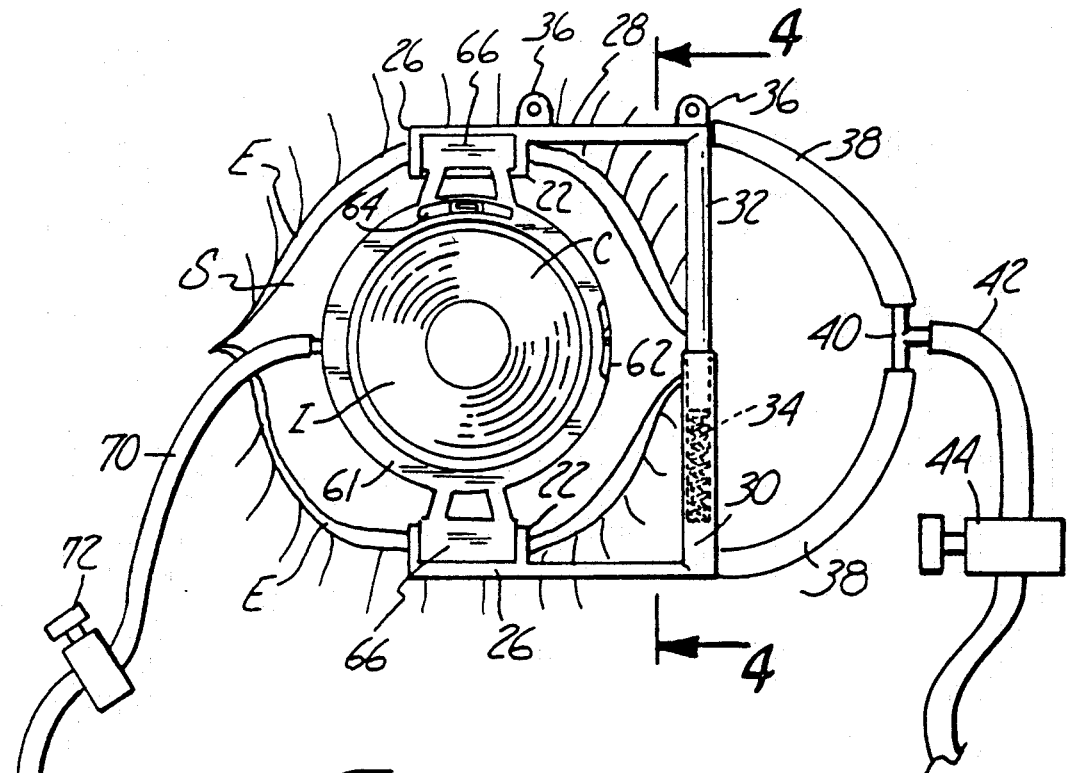
FIG. 1 is a top, plan view of the device secured to the eye of a patient.
Figure 2:
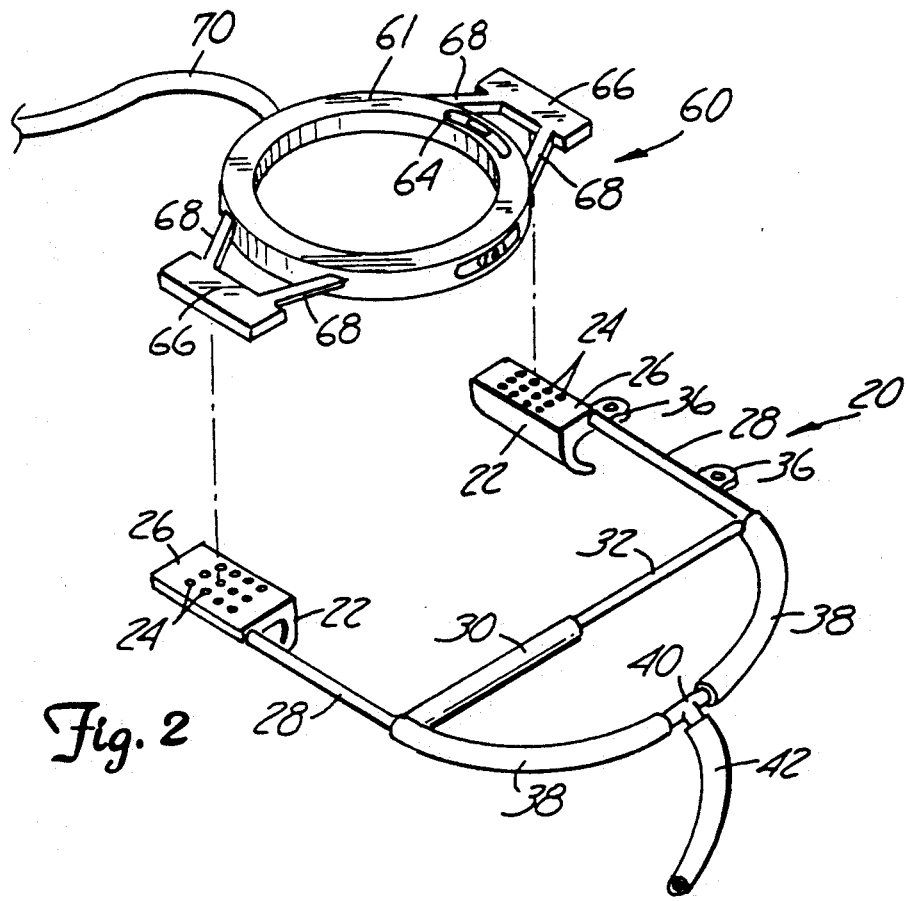
FIG. 2 is a perspective view of the device of the invention.

The fixation device of the invention includes a speculum 20 have a pair of opposed blades 22 for holding the eyelids E open against the bony orbit B of a patient. The blades 22 are carried by a pair of tubes 28 (or equivalent structure) which in turn are secured to one another in a fashion so as to provide a biasing force to urge the blades 22 away from one another. In the drawings, the tubes 28 are so connected by telescoping tubes 30 and 32. As shown by phantom lines in FIG. 1, the telescoping tubes include a spring 34 carried within the outer tube 30 to bias the inner tube 32 outwardly of the outer tube 30, therefore urging the blades 22 apart to securely engage the blades 22 against the bony orbit B. Alternately, any other suitable biasing mechanism may be used to provide the requisite force for biasing the blades 22 against the bony orbit B.

Figure 3:
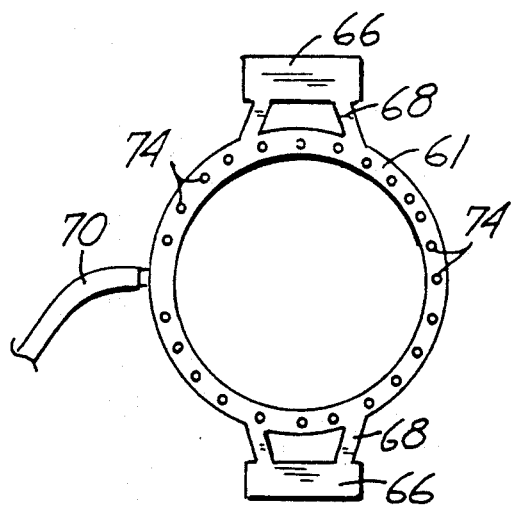
FIG. 3 is a bottom view of the fixation ring of the invention.

The fixation ring 60 of the invention includes an annular fixation portion 61 which is to be positioned concentrically about the cornea C of the eye. As shown in FIG. 3 (which is a bottom view of the fixation ring 60), the bottom surface of the annular fixation portion 61 includes a plurality of holes 74 which permit vacuum to be drawn therethrough to secure the ring against the surface of the eye. Holes 74 communicate with vacuum tube 70, which may be attached to any suitable vacuum source, such as a large syringe with a spring plunger, or other suitable vacuum supply. Preferably, the vacuum tube 70 also includes a release valve 72 which can be manually actuated to alternately supply or release the vacuum in the fixation ring.

Means is provided for fixating the ring 60 with respect to the speculum 20. In a preferred embodiment illustrated in the drawings, the blades 22 of the speculum 20 each include a flat top surface 26 having holes 24 therein. Holes 24 in turn are connected through interior passageways in tubes 28 to vacuum tubes 38, which in turn are connected by a T-connector 40 to a proximal vacuum tube 42. Again, a release valve 44 may be provided in the proximal vacuum tube 42 to allow control over the vacuum applied to the vacuum holes 24 in the blades 22. The fixation ring 60 in turn includes corresponding attachment plates 66, secured to the annular portion 61 by trusses 68 (or other suitable attachment). Desirably, the attachment plate 66 is somewhat larger than the field of vacuum holes 24 on the speculum blade 22, so that the fixation ring 60 can be adjusted with respect to the speculum (within reasonable limits) without leaving any of the vacuum holes 24 uncovered.

Alternate equivalent means could also be employed to secure the fixation ring 60 to the speculum 20. For example, the vacuum could be supplied through conduits and holes in the fixation ring rather than through the speculum. Alternately, the vacuum system could be replaced by an electromagnet carried in either the speculum blades 22 or the attachment plates 66, the electromagnet being activatable by a conveniently located switch. Further, mechanical attachment mechanisms could be used, such as hook and loop attachment, or even pressure sensitive or quick setting adhesives. Regardless of the means utilized, the important feature is that the fixation ring be able to be secured to the speculum once the ring has been properly positioned on the eye and the eye is in its proper orientation.

Figure 4:
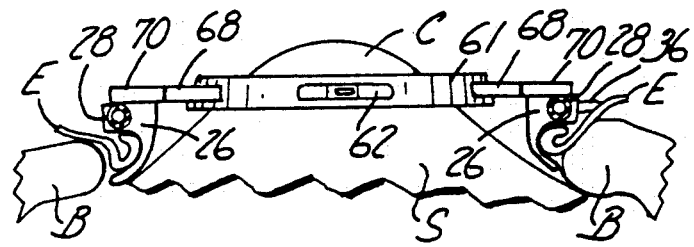
FIG. 4 is a cross-sectional view of FIG. 1 taken along line 4—4 thereof.
Figure 5:
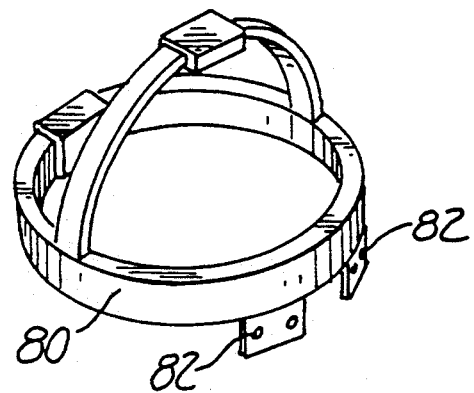
FIG. 5 is a somewhat schematic drawing of a headband usable with the device of the invention.

One or more levels may be provided on the fixation ring to indicate the orientation of the ring. In a preferred embodiment illustrated in the drawings, two such levels 62 and 64 are provided, the levels illustrated being of the colored-liquid/bubble type (although electronic levels or levels of any other type may also be utilized). Such levels are most useful during surgical techniques in which the patient is lying prone on his back, and the eye is to be fixated with the plane of the iris being perfectly horizontal (such as during excimer laser keratectomy). During such procedure, the surgeon typically utlizes an operating microscope through which the level 64 (on the top surface of the annular fixation portion 61 of the fixation ring 60) is visible. Also, typically such excimer lasers include a camera giving a video image of a side view of the profile of the eye, such as is shown in FIG. 4. Placement of a level 62 on the side of the fixation ring 60 therefore would make this level 62 visible in such video image. By centering the fixation ring 60 coaxially of the cornea, the surgeon can then use the levels to determine when a plane tangent to the apex of the cornea is exactly horizontal, at which time the surgeon can activate the mechanism which secures the fixation ring with respect to the speculum, thereby securing the eye in the optimum position.

In other procedures, such as laser photocoagulation or foreign body removal from the cornea, the patient is normally seated upright in front of a slit lamp or laser. In such cases, the eyelets 36 (or equivalent connective elements) on the tubes 28 can be attached to a support mechanism worn by the patient to help support the weight of the speculum. For example, the eyelets 36 can be attached to a complimentary tab 820N a headband 80 similar to an indirect ophthalmoscope.

In use the surgeon first locates the patient in the position for the procedure, such as laying prone or sitting in a chair for a upright procedure. The speculum 20 is then inserted to hold the eyelids E open, the speculum being seated against the bony orbit B of the patient (as shown in FIG. 4). The fixation ring 60 is then placed on and centered on the eye about the cornea C so that it is generally coaxial of the cornea. Typically the ring 60 will actually rest on the episcleral/conjunctival surface near the limbus. The fixation ring is secured to the eye by actuation of vacuum attached to the vacuum tube 70 (as by actuating valve 72 or another mechanism associated with the vacuum source). The surgeon then asks the patient to look directly at a point of light or similar target to properly orient the patient's eye with respect to the laser or other instrument to be utilized by the surgeon. If the levels 62, 64 are utilized on the fixation ring, the surgeon can reference them to obtain proper orientation and alignment of the patient's eye. When the surgeon determines that the alignment is proper, the attachment means between the speculum and the fixation ring is actuated (as by supplying vacuum through vacuum tubes 42 and 38, by actuating the electromagnet, or similar mechanism). The fixation ring 60 is thereby secured to the speculum to substantially immobilize the patient's eye for the procedure to be performed.

Both of the physician's hands are then free to operate other surgical instruments and/or to help hold the patient's head still during the surgical procedure (oftentimes the patient's head will be substantially immobilized by tape, a three-point fixation device, commercially available suction devices, or the like, but the surgeon may augment the use of such devices by holding onto the patient's head with at least one of his hands, depending upon the procedure being performed).

It is a distinct advantage of the invention that the fixation device is merely anchoring the eye with respect to the bony orbit B of the patient's head. That is, the device is not physically secured to any external equipment. Thus, in an emergency (such a if the patient would panic or otherwise find it necessary to suddenly move his head substantially), no damage or trauma would be caused to the patient's eye as the device would maintain its position. This is in sharp contrast to the mechanisms contemplated in, e.g., U.S. Pat. No. 4,718,418 (referred to above).

The invention also ensures that any modest change in the intraocular pressure of the eye is both controlled and predictable——unlike the prior art methods (such as grasping the eye with a forceps) which can induce erratic changes in intraocular pressure and concomitant distortion of the corneal topography.

The device of the invention can be manufactured from any suitable materials. Desirably, the device can be made of suitable plastics and/or metals and can be cheaply manufactured so as to be disposable, thereby eliminating the need for repeat sterilization. Both the speculum and the fixation ring can also be manufactured in different diameters for use in different sized eyes. If desired, the bottom surface of the fixation ring can be made out of silicone to assure a good seal against the eye and to minimize any trauma to the ocular surface.

While a preferred embodiment of the present invention has been described, it should be understood that various changes, adaptations and modifications may be made therein without departing from the spirit of the invention and the scope of the appended claims.

What is claimed is:

1. An ophthalmic instrument of fixating a patient's eye during an ophthalmic procedure, comprising:
   a speculum including a pair of opposed blades securable against the patient's bony orbit;
   a fixation ring including means for fixating the ring with respect to the eye; and attachment means for adjustably attaching the ring to the blades of the speculum and permitting lateral and longitudinal adjustment of the fixation ring with respect to the speculum after the fixation ring is fixated with respect to the eye.

2. The instrument of claim 1 wherein the attachment means includes a pair of attachment plates secured to the fixation ring.

3. The instrument of claim 2 wherein the attachment means further comprises vacuum means connected to the speculum for securing the attachment plates to the speculum.

4. An ophthalmic instrument for fixating a patient's eye during an ophthalmic procedure, comprising:
   a speculum securable against the patient's bony orbit,
   a fixation ring including means for fixating the ring with respect to the eye; and attachment means for adjustably attaching the ring to the speculum, the attachment means including a pair of attachment plates secured to the fixation ring and vacuum means connected to the speculum for securing the attachment plates to the speculum, the speculum including a pair of opposed blades, each blade a generally flat top surface having holes therein associated with the vacuum means, the holes being located to provide vacuum to secure the attachment plates to the speculum blades when the vacuum means is actuated.

5. The instrument of claim 1 including further attachment means for securing the speculum to a head band worn by the patient.

6. The instrument of claim 1 wherein the opposed blades engage the patient's eyelid against the patient's bony orbit, the blades being biased away from one another.

7. The instrument of claim 1 wherein the means for fixating the ring with respect to the eye comprises a vacuum source and passageway defined in the fixation ring for communicating the vacuum source with a bottom surface of the ring securable against the patient's eye.

8. An ophthalmic instrument for fixating a patient's eye during an ophthalmic procedure, comprising:
   a speculum securable against the patient's bony orbit, the speculum including a pair of opposed blades for engaging the patient's eyelid against the patient's bony orbit, and means for biasing the blades away from one another, each blade including a generally flat top surface having holes therein communicatable with a vacuum source;
   a fixation ring including fixation means for fixating the ring with respect to the eye, the fixation means comprising a vacuum source and passageways defined in the fixation ring for communicating the vacuum source with a bottom surface of the ring securable against the patient's eye; and
   attachment means for adjustably attaching the ring to the speculum, the attachment means including a pair of attachment plates secured to the fixation ring, and a second vacuum source connected to the speculum for providing vacuum in the holes in the speculum blades to secure the attachment plates to the speculum blades when the vacuum means is actuated.

9. An ophthalmic instrument for fixating a patient's eye during an ophthalmic procedure, comprising:
   a fixation ring including means for fixating the ring to the eye; and
   a level carried on the fixation ring for indicating orientation of the ring with respect to a reference plane.

10. The instrument of claim 9 wherein the fixation ring includes a top and an outer side, and further comprising two such levels carried on the fixation ring, one being visible from the top of the ring, and the other being visible from a side of the ring.

11. The instrument of claim 10 wherein the two levels are oriented generally perpendicularly with respect to one another.

12. The instrument of claim 9 wherein the level comprises a liquid bubble-type level.

13. The instrument of claim 9 including two such levels located generally perpendicular to one another for indicating orientation of the ring with respect to two generally perpendicular lines.

14. An ophthalmic instrument for fixating a patient's eye during an ophthalmic procedure, comprising:
   a speculum including a pair of opposed blades securable against the patient's bony orbit;
   a fixation ring including means for fixating the ring with respect to the eye; and
   attachment means for adjustably attaching the ring to the speculum and permitting lateral and longitudinal adjustment of the fixation ring with respect to the speculum after the fixation ring is fixated with respect to the eye.

15. A method of fixating a patient's eye during an ophthalmic procedure, comprising:
   securing a speculum having a pair of opposed blades against the patient's bony orbit;
   positioning a fixation ring on the surface of the patient's eye generally coaxially of the patient's cornea and then securing the ring to the surface of the patient's eye; and
   allowing the patient to move his/her eye to properly position it with respect to the speculum, and then securing the fixation ring to the speculum.

* * * * *